(12) United States Patent
Murty et al.

(10) Patent No.: US 8,945,615 B2
(45) Date of Patent: *Feb. 3, 2015

(54) CONTROLLED RELEASE BUDESONIDE MINITABLETS

(75) Inventors: Mummini Aruna Murty, Morgantown, WV (US); Boyong Li, Morgantown, WV (US)

(73) Assignee: Mylan Pharmaceuticals Inc., Morgantown, WV (US)

( * ) Notice: Subject to any disclaimer, the term of this patent is extended or adjusted under 35 U.S.C. 154(b) by 1126 days.

This patent is subject to a terminal disclaimer.

(21) Appl. No.: 12/372,333

(22) Filed: Feb. 17, 2009

(65) Prior Publication Data

US 2010/0209500 A1 Aug. 19, 2010

(51) Int. Cl.
*A61K 9/52* (2006.01)
*A61K 9/24* (2006.01)
*A61K 31/58* (2006.01)
*A61K 9/20* (2006.01)
*B05D 1/02* (2006.01)
*A61K 9/28* (2006.01)
*A61K 9/48* (2006.01)

(52) U.S. Cl.
CPC ............. *A61K 9/2072* (2013.01); *A61K 9/2846* (2013.01); *A61K 9/4808* (2013.01)
USPC ........... 424/457; 424/472; 424/465; 514/174; 427/2.16

(58) Field of Classification Search
None
See application file for complete search history.

(56) References Cited

U.S. PATENT DOCUMENTS

| | | | |
|---|---|---|---|
| 5,643,602 A * | 7/1997 | Ulmius | 424/462 |
| 5,840,332 A | 11/1998 | Lerner et al. | |
| 5,849,327 A | 12/1998 | Berliner et al. | |
| 5,916,593 A * | 6/1999 | de Haan et al. | 424/465 |
| 6,984,404 B1 | 1/2006 | Talton et al. | |
| 2005/0112201 A1 | 5/2005 | Baichwal et al. | |
| 2005/0158385 A1 | 7/2005 | Verreck et al. | |
| 2006/0057200 A1 | 3/2006 | Schaeffler | |
| 2006/0188563 A1 * | 8/2006 | Sato et al. | 424/451 |
| 2006/0204576 A1 | 9/2006 | Petereit et al. | |

FOREIGN PATENT DOCUMENTS

| | | |
|---|---|---|
| EP | 1607087 A1 | 12/2005 |
| WO | 9107172 A1 | 5/1991 |
| WO | 0076478 A1 | 12/2000 |
| WO | 03080032 A2 | 10/2003 |

OTHER PUBLICATIONS

AquaCoatECD30, web.archive.org/web/20061015221853/http://www.fmcbiopolymer.com/Portals/bio/content/Docs/AquaCoat+ECD+7706+.pdf, (available online Oct. 15, 2006).*
Ansel et al. In Pharmaceutical Dosage forms and Drug Delivery Systems 7th Edition, Lippincott, Williams and Wilkins Ed., pp. 209-213 (1999).*
Krishnamacher Y et al., Development of pH- and time-dependent oral microparticles to optimize budesonide delivery to ileum and colon, A service of the U.S. National Library of Medicine and the National Institutes of Health, Jun. 20, 2007, 338(1-2):238-47.
International Search Report and Written Opinion pertaining to International application No. PCT/US2009/037331 dated Oct. 13, 2009.

* cited by examiner

*Primary Examiner* — Dennis Heyer

(57) ABSTRACT

Embodiments of a controlled release minitablet comprise an extended release core and an optional pH dependent delayed release coating thereon, wherein the extended release core comprises budesonide, a carrier, an extended release polymer, and an acid. The budesonide may be embedded in the extended release polymer to facilitate extended release of the budesonide upon administration.

22 Claims, 2 Drawing Sheets

CONTROLLED RELEASE BUDESONIDE MINITABLETS

TECHNICAL FIELD

Embodiments of the present invention are generally directed to budesonide formulations, and are specifically directed to controlled release budesonide minitablets.

BACKGROUND

Budesonide's chemical name is 16,17-(butylidenebis(oxy))-11,21-dihydroxy-,(11-β,16-α)-pregna-1,4-diene-3,20-dione, and its chemical structure is shown, below:

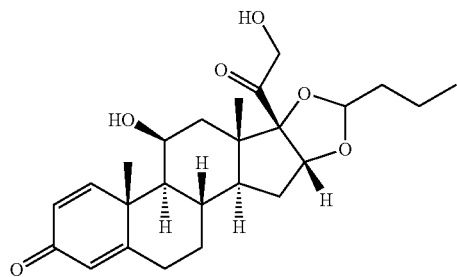

Budesonide is the active ingredient in a gastrointestinal pharmaceutical formulation directed to the treatment of mild to moderate active Crohn's disease involving the ileum and/or the ascending colon, and the maintenance of clinical remission of mild to moderate active Crohn's disease involving the ileum and/or the ascending colon. Some conventional formulations utilize a non-pareil seed and two coatings, wherein the first coating comprises budesonide embedded in the extended release polymer, and the second coating is a pH dependent coating for delayed release. Alternative conventional formulations include a pellet core comprising budesonide, and at least two coatings thereon. However, the conventional formulations have numerous limitations. For example, it is a lengthy and difficult process to control the pellet coating process, because the pellets tend to agglomerate. Moreover, extended release coatings on pellets, especially coatings involving ethylcellulose, require an additional curing step to prevent a decrease in dissolution rate over time.

Consequently, there is a need for improved budesonide formulations which are easier to manufacture, while maintaining a desirable dissolution profile.

SUMMARY

According to one embodiment, a controlled release minitablet is provided. The minitablet comprises an extended release core and an optional pH dependent delayed release coating thereon. The extended release core comprises budesonide, a carrier, an extended release polymer, and an acid, wherein the budesonide may be embedded in the extended release polymer to facilitate extended release of the budesonide upon administration.

According to yet another embodiment, a method of making controlled release minitablets is provided. The method comprises feeding a carrier into a fluidized bed reactor, spraying a suspension comprising budesonide, acid, and an extended release polymer onto the carrier to produce a granulated mixture, compressing the granulated mixture into extended release cores, and coating the extended release cores with a pH dependent delayed release coating to produce a controlled release minitablet.

These and additional features provided by the embodiments of the present invention will be more fully understood in view of the following detailed description, in conjunction with the drawings.

BRIEF DESCRIPTION OF THE DRAWINGS

The following detailed description of specific embodiments of the present invention can be best understood when read in conjunction with the drawings enclosed herewith.

Figure 1:
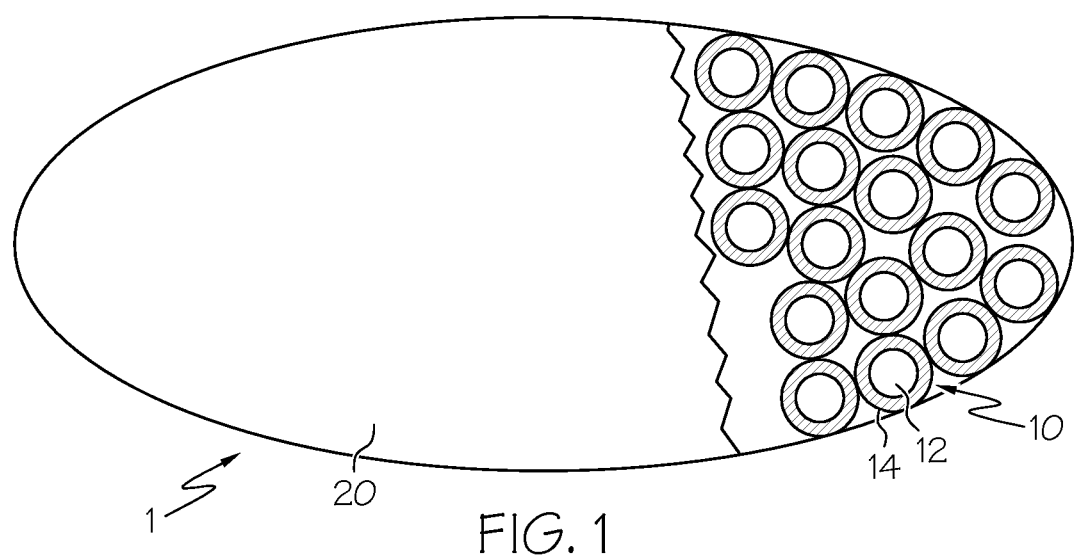
FIG. 1 is a schematic cross-sectional view of a capsule comprising controlled release minitablets according to one or more embodiments of the present invention.

The embodiments set forth in the drawings are illustrative in nature and not intended to be limiting of the invention defined by the claims. Moreover, individual features of the drawings and invention will be more fully apparent and understood in view of the detailed description.

DETAILED DESCRIPTION

Embodiments of the present invention are directed to budesonide formulations containing controlled release minitablets (e.g., extended release) that contain the budesonide active ingredient, the carrier, an acid, and the extended release polymer. The budesonide formulations also comprise a pH dependent coating disposed over the minitablet, which delays release of the budesonide from the minitablets. In combining extended release minitablets and an optional delayed release pH dependent coating thereon, the present inventors have recognized that combining multiple release profiles yields an advantageous dissolution profile for the active budesonide ingredient. Depending on the amount of extended-release polymer, the amount of acid and the amount of disintegrant in the core, the release can be extended, for example, from 6 hours to more than 12 hours. The rate of release of drug from the core is decreased with: 1) increasing amounts of extended release polymer, 2) increasing amount of acid; and 3) decreasing the amount of disintegrant in the core.

The pH delayed release coating may be optimized to stay intact as long as the surrounding medium has pH of about 5.5 or less. Because the delayed release coating is pH dependent, substantially no drug will be released in the stomach, which has a pH of below 5.5. When the coated mini tablet leaves the stomach, the higher pH in the small intestine will dissolve the delayed release coating allowing controlled release of the drug from the core. Therefore, the delay in release is the residence time in the stomach.

Referring to the cross-sectional view of FIG. 1, a capsule formulation 1 comprising a plurality of controlled release minitablets 10 is provided. As shown, the capsule formulation 1 may comprise any suitable encapsulant 20 known to one of ordinary skill in the art. For example, and not by way of limitation, the encapsulant 20 may comprise gelatin, carbohydrate, or combinations thereof. Although the embodiment of FIG. 1 illustrates a capsule embodiment 1, it is contemplated that other delivery vehicles may also be utilized, e.g., a tablet.

Referring again to FIG. 1, the minitablet 10 comprises an extended release core 12 and a pH dependent delayed release coating 14 over the extended release core 12. The extended release core 12 comprises budesonide, a carrier, an extended release polymer, and an acid. These components of the extended release core may be present in any suitable mixture familiar to one of ordinary skill in the art e.g., a homogeneous mixture or a multi-phase emulsion. In a further embodiment, the budesonide active may be embedded in an extended release polymer matrix to better facilitate the extended release of the budesonide upon administration.

Numerous compositions are contemplated for the extended release polymer. The extended release polymer may comprise at least one water insoluble polymer, or may, in another embodiment, comprise a mixture of at least one water insoluble polymer and at least one water soluble polymer. Water insoluble polymers may include various compositions, for example, ethylcellulose or its aqueous suspension system such as Aquacoat ECD and co-polymers of acrylic and methacrylic acid esters (Eudragit® RS or RL). Water soluble polymers may include various compositions, for example, polyvinylpyrrolidone or hypromellose. In one exemplary embodiment, the extended release polymer may be selected from the group consisting of polymethacrylates, cellulose, polymeric derivatives of acetate, polymeric derivatives of citrate, and mixtures thereof. In further exemplary embodiments, the extended release polymer may comprise ethyl cellulose, cellulose acetate, cellulose acetate butyrate, ethylene vinylacetate copolymer, polyvidone acetate, polyvinyl acetate, ethyl acrylate/methyl methacrylate copolymer, ammonia methacrylate copolymer, methylcellulose, hydroxypropyl cellulose, or combinations thereof. In an exemplary embodiment, the extended release polymer comprises a mixture of Aquacoat ECD, (a 30% by weight aqueous dispersion of ethylcelluose polymer commercially available from FMC Biopolymer) and acetyltributyl citrate (CAS 77-90-7 sold as a carrier or plasticizer).

Acetyltributyl citrate is not an extended release polymer. It is a plasticizer often used along with the extended release polymer to form the extended-release film and make it stronger and more elastic. The extended release polymer system consists of the extended-release polymer (Aquacoat ECD) and a plasticizer (acetyltributyl citrate). While the examples use acetyltributyl citrate as its plasticizer, other suitable plasticizers are contemplated herein, for example, acetyltriethyl citrate, dibutyl sebacate, tri-n-butyl citrate, and triethyl citrate.

The extended release polymer may be present in various amounts suitable to achieve extended release of the budesonide active ingredient. For example, the extended release polymer and the budesonide may be present in the minitablet 10 at a ratio by weight of about 0.1:1 to about 20:1, or from about 1.1 to about 10.1. In a further embodiment, the ratio of extended release polymer to budesonide is 3.75, which equates to 3.75 mg of extended-release polymer (e.g., 3 mg of ethyl cellulose and 0.75 mg of Acetyltributyl citrate) for every 1 mg of budesonide.

The carrier of the controlled release minitablet may comprise any pharmaceutically acceptable material, for example, substantially water soluble or water swellable inert material. This includes, but is not limited to, sugar, starch, microcrystalline celluloses and combinations of these materials. The carrier may be present in the minitablet 10 at an amount of from about 25 to about 95% by weight of the carrier, or from about 75 to about 85% by weight of the carrier.

Figure 2:
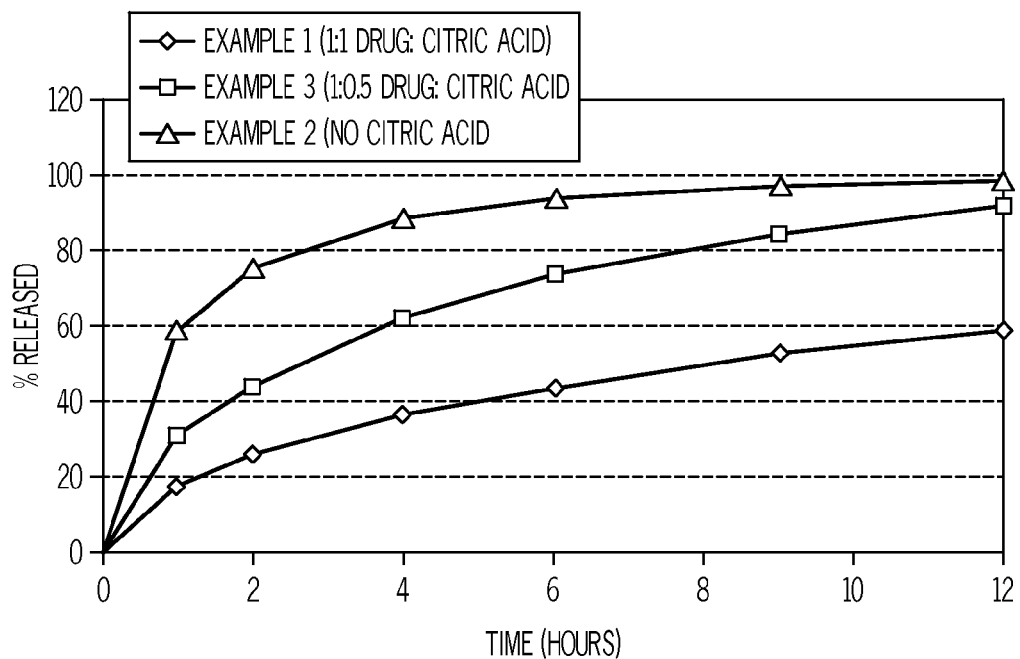
FIG. 2 is a graphical illustration demonstrating the effect of citric acid on the drug release of budesonide according to one or more embodiments of the present invention.

Referring again to FIG. 1, the minitablet 10 may also comprise an acid or various other optional excipients familiar to one of ordinary skill in the art. The acid may include citric acid, tartaric acid, acetic acid, ascorbic acid, malic acid, or combinations thereof. In one embodiment, the acid may comprise citric acid. Although various compositions are possible, the acid and budesonide may be present in the minitablet at a ratio by weight of about 0.1:1 to about 10:1, or about 0.1:1 to about 2:1. As illustrated in FIG. 2 and the Examples below, increasing the amount of acid in the minitablet 10 may extend the release time of the budesonide active ingredient. Visual observations of the mini-tablets with different levels of citric acid reveal that citric acid inhibits the disintegration of the core and thereby decreases the rate of drug release.

Figure 3:
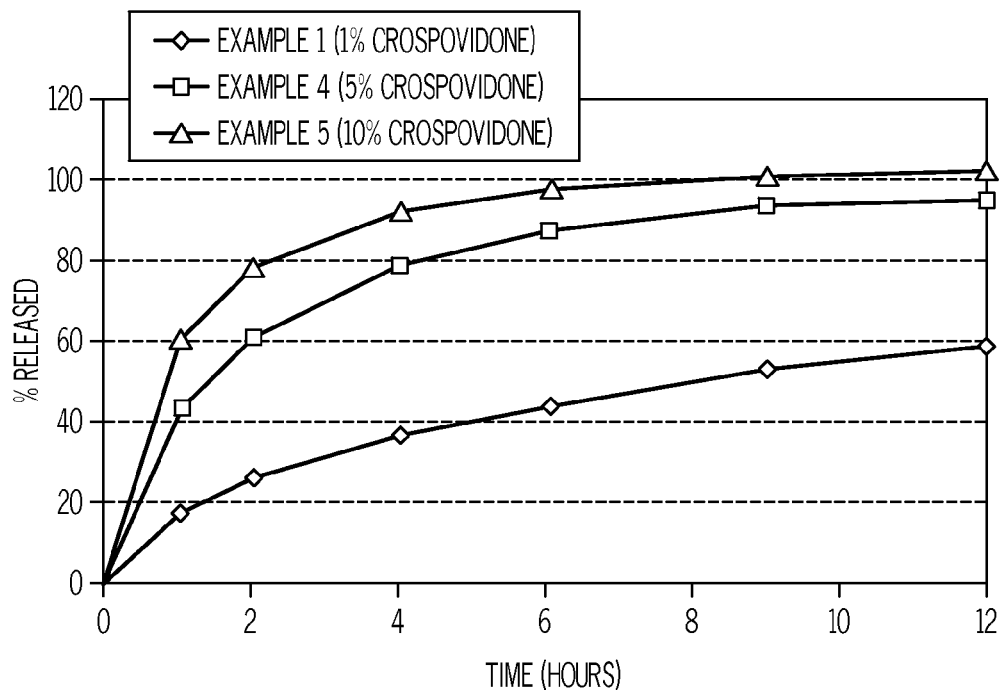
FIG. 3 is a graphical illustration demonstrating the effect of disintegrant on the drug release of budesonide according to one or more embodiments of the present invention.

Moreover, the minitablet 10 may also optionally contain lubricants, disintegrants, or other pharmaceutically acceptable excipients familiar to one of ordinary skill in the art. The disintegrant may aid in the delivery of the budesonide upon administration into the body. As shown in FIG. 3 and detailed in the Examples below, increasing the amount of disintegrant may increase the release rate of the budesonide active ingredient. The disintegrant helps in the disintegration of the extended release core, thereby allowing controlled release of the drug. Increasing the amount of disintegrant will increase the rate of drug release and thereby will reduce the extended release time. However, without disintegrant, the core will not disintegrate easily and no or very little drug will be released, thus the amount of disintegrant must be optimized to achieve extended release. Disintegrants may include alginic acid, croscarmellose, crospovidone, starch, microcystalline cellulose, hydroxypropyl celluloses, e.g., low-substituted hydroxypropyl cellulose, sodium starch glycolate, or combination thereof. In one exemplary embodiment, the disintegrant comprises crospovidone.

While various compositions are contemplated herein, the lubricant may be included in the composition to help prevent the minitablets from sticking to the equipment during processes such as tabletting. The lubricant may include hydrogenated vegetable oil, vegetable based fatty acids, magnesium stearate, stearic acid, sodium stearyl fumarate, or combinations thereof. In one exemplary embodiment, the lubricant comprises magnesium stearate.

Referring to FIG. 1, the minitablet 10 may also comprise a pH dependent delayed release 14 coating over the extended release core 12. In one exemplary embodiment, the pH dependent delayed release coating may be selected from a group of anionic carboxylic polymers which are soluble at a pH of about 4 to about 8 and insoluble at a pH of about 1 to about 3. In one or more additional exemplary embodiments, the pH dependent delayed release coating comprises cellulose acetate phthalate, cellulose acetate trimellitate, hydroxypropylmethylcellulose phthalate, polyvinyl acetate phthalate and acrylic acid polymers, and combinations thereof. Although other amounts are contemplated herein, the minitablet 10 may comprise from about 1 to about 50% by weight of the pH dependent delayed release coating, or from about 4 to about 10% by weight of the pH dependent delayed release coating. As stated above, the delayed release coating stays intact as long as the surrounding medium has pH of 5.5 or less, and will only release the drug at higher pH values. In operation, substantially no drug will be released in the low pH stomach. However, when the coated minitablet leaves the stomach and enters the bowel, the higher pH in the small intestine will dissolve the delayed release coating allowing controlled release of the drug from the core.

Various sizes and shapes for the minitablets are contemplated herein. For example, the minitablets may comprise a diameter of from about 1 mm to about 7.8 mm, or from about 1.5 mm to about 2.5 mm. By minimizing the surface area of the minitablets, the coating time is decreased.

Various processes for producing the minitablets are contemplated herein. For example, a carrier (e.g., lactose) may be sprayed with a suspension comprising budesonide and an extended release polymer inside a reacting vessel (e.g., a fluidized bed reactor) to form a granulated mixture. In addition, the suspension may also include an acid and other excipients. The granulated mixture may then be milled and blended with other optional ingredients (e.g., lubricants and disintegrants), at which point, the blend is compressed into extended release cores 12 as shown in FIG. 1. To produce the pH dependent delayed coating over the extended release cores 12, a coating suspension comprising one or more anionic carboxylic polymers is applied thereon. The present process minimizes processing steps and facilitates better control of the wet granulation and compression process steps for the core minitablets as well as the coating step for the delayed release coating. Additionally, the present minitablet composition reduces the tendency for sticking during coating, thereby allowing for higher spray rates and decreased coating time. Moreover, the present process eliminates the need for a curing step. For a given amount, mini-tablets (~2.25 mm in diameter) have less surface area than beads (0.6-1.2 mm). Therefore less delayed release coating material is required for mini-tablets to achieve acid resistance as compared to beads. Generally more than 10% coating weight gain is required for beads and about 4-6% weight gain is required for mini-tablets. The processing time for delayed release coating is reduced since less coating needs to be applied for mini-tablets as compared to beads. Another reason for decreased processing time is the increased spray rates for coating mini-tablets. The spray rate for pellets is generally around 10-15 g/min, whereas for minitablets it is around 25-30 g/min.

The following method steps illustrate exemplary embodiments for producing the controlled release minitablets using various compositions and provides a comparison of these compositions:

Example 1

In a fluidized bed, 716.9 g of lactose was sprayed with a suspension (17.6% solid content) composed of 12.0 g of Budesonide, 12.0 g of citric acid, 104.0 g of Aquacoat ECD, 7.8 g of acetyltributyl citrate and 0.12 g of Polysorbate 80. The ratio of Aquacoat ECD and acetyltributyl citrate to Budesonide was 3.25:1. The resulting granules were milled. 488.2 g of the milled granules were blended with 2.5 g of colloidal silicon dioxide, 5.0 g of crospovidone and 5.0 g of magnesium stearate/sodium lauryl sulfate. The blend was compressed into extended release cores.

In a coating pan, 480.7 g of the extended release cores were coated with the enteric coating suspension (20% solid content) to a theoretical weight gain of 10%. The enteric coating suspension consisted of 120.0 g of Eudragit L30D-55, 5.4 g of triethyl citrate, 6.0 g of talc, 0.48 g of Polysorbate 80 and 0.12 g of sodium hydroxide. The coated minitablets were blended with 1.47 g of talc.

The compositions of the Example 1 coated minitablet may then be encapsulated into a capsule, wherein the capsule may comprise the composition listed in Table 1 below.

TABLE 1

| Ingredient | mg/unit |
| --- | --- |
| Budesonide | 3.0 |
| Citric acid | 3.0 |
| Aquacoat ECD | 7.80 |
| Acetyltributyl Citrate | 1.95 |
| Polysorbate 80 | 0.23 |
| Colloidal Silicon Dioxide | 1.0 |
| Magnesium Stearate/Sodium Lauryl Sulfate | 2.0 |
| Crospovidone | 2.0 |
| Eudragit L3OD-55 | 15.0 |
| Triethyl Citrate | 2.25 |
| Talc | 2.5 |
| Sodium Hydroxide | 0.05 |
| Lactose | remaining quantity |
| Total | 220.6 |

Example 2

The formulation and process are the same as Example 1 except that there was no citric acid in the formulation and the core minitablets were coated to a theoretical weight gain of 8% delayed release coating in a fluid bed equipped with a rotor.

Example 3

The formulation and process are the same as Example 1 except that the ratio of budesonide to citric acid was 1 to 0.5 and the core minitablets were coated to a theoretical weight gain of 6% delayed release coating.

To demonstrate the effect of citric acid on dissolution, the graphical illustration of FIG. 2 is provided herein. In the example, the controlled release minitablets were treated in two stages: 1) an acid stage wherein the controlled release minitablets were placed in a solution of 0.1 N HCl for (2) two hours; and 2) a pH buffered stage wherein the controlled release minitablets were dissolved in a pH 6.8 buffered solution using USP Paddles at 100 rpm. As shown in the graphical illustration of FIG. 2, the Example 1 (1:1 ratio of budesonide:citric acid) has released about 60% of the budesonide after 12 hours whereas Example 2 (no citric acid) has released about 100% of the budesonide after 12 hours. Similarly, Example 3 (1:0.5 ratio of budesonide:citric acid) has released slightly less of the budesonide (almost 100%) after 12 hours. As shown, increasing the amount of citric acid slows the release of budesonide, thereby extending the release of budesonide to greater than 12 hours.

Example 4

The formulation and process are the same as Example 1 except that the amount of crospovidone was 10 mg/unit (5% crospovidone) and the core minitablets were coated to a theoretical weight gain of 6% delayed release coating.

Example 5

The formulation and process are the same as Example 1 except that the amount of crospovidone was 20 mg/unit (10% crospovidone) and the core minitablets were coated to a theoretical weight gain of 6% delayed release coating in a fluid bed equipped with a rotor.

To demonstrate the effect of disintegrant on dissolution, the graphical illustration of FIG. 3 is provided. As shown in FIG.

3, Example 1 (1% crospovidone) has released about 60% of the budesonide after 12 hours whereas Example 5 (10% crospovidone) has released about 100% of the budesonide after 12 hours. As shown, increasing the amount of crospovidone disintegrant increases the release rate of budesonide.

For the purposes of describing and defining the present invention it is noted that the terms "substantially" and "about" are utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these aspects of the invention.

What is claimed is:

1. A controlled release minitablet comprising an extended release core and a pH dependent delayed release coating thereon, wherein:
    the extended release core comprises a homogeneous mixture of budesonide, a carrier, at least one extended release polymer, a plasticizer, and an acid;
    the pH dependent delayed release coating comprises an anionic carboxylic polymer that is soluble in water at a pH of about 4 to about 8 and insoluble at a pH of about 1 to about 3; and
    the pH dependent delayed release coating is in direct contact with the homogeneous mixture of the extended release core.

2. The controlled release minitablet of claim 1 wherein the budesonide is embedded in the extended release polymer.

3. The controlled release minitablet of claim 1 wherein the at least one extended release polymer is selected from the group consisting of water insoluble polymers, water soluble polymers, and mixtures thereof.

4. The controlled release minitablet of claim 1 wherein the at least one extended release polymer comprises a member selected from the group consisting of ethyl cellulose, cellulose acetate, cellulose acetate butyrate, ethylene vinylacetate copolymer, polyvidone acetate, polyvinyl acetate, ethyl acrylate/methyl methacrylate copolymer, ammonia methacrylate copolymer, methylcellulose, hydroxypropyl cellulose, and combinations thereof;
    wherein the acid is selected from the group consisting of citric acid, tartaric acid, acetic acid, ascorbic acid, malic acid, and combinations thereof; and
    wherein the carrier comprises sugar, starch, microcrystalline celluloses, or a combination of these materials.

5. The controlled release minitablet of claim 1 wherein the extended release polymer and budesonide are present in the minitablet at a ratio by weight of about 0.1:1 to about 20:1, respectively.

6. The controlled release minitablet of claim 1 wherein the acid and budesonide are present in the minitablet at a ratio by weight of about 0.1:1 to about 10:1, respectively.

7. The controlled release minitablet of claim 1 wherein the weight of the carrier is from about 25% to about 95% of the total weight of the controlled release minitablet.

8. The controlled release minitablet of claim 1 wherein the weight of the pH dependent delayed release coating is from about 1 to about 50% of the total weight of the controlled release minitablet.

9. The controlled release minitablet of claim 1 wherein the pH dependent delayed release coating comprises at least one member selected from the group consisting of cellulose acetate phthalate, cellulose acetate trimellitate, hydroxypropylmethylcellulose phthalate, polyvinyl acetate phthalate, acrylic acid polymers, and combinations thereof.

10. The controlled release minitablet of claim 1 wherein the minitablet has a diameter of from about 1 mm to about 7.8 mm.

11. The controlled release minitablet of claim 1 wherein the plasticizer is selected from the group consisting of acetyltributyl citrate, acetyltriethyl citrate, dibutyl sebacate, tri-n-butyl citrate, and triethyl citrate.

12. The controlled release minitablet of claim 1 wherein the plasticizer is acetyltributyl citrate.

13. The controlled release minitablet of claim 12 wherein the extended release polymer is ethylcellulose polymer.

14. A controlled release minitablet comprising an extended release core and a pH dependent delayed release coating thereon, wherein:
    the extended release core comprises a homogeneous mixture of budesonide, a carrier, at least one extended release polymer, a plasticizer, and an acid
    the pH dependent delayed release coating comprises at least one anionic carboxylic polymer chosen from cellulose acetate phthalate, cellulose acetate trimellitate, hydroxypropylmethylcellulose phthalate, polyvinyl acetate phthalate, acrylic acid polymers, and combinations thereof; and
    the pH dependent delayed release coating is in direct contact with the homogeneous mixture of the extended release core.

15. The controlled release minitablet of claim 14 wherein the plasticizer is selected from the group consisting of acetyltributyl citrate, acetyltriethyl citrate, dibutyl sebacate, tri-n-butyl citrate, and triethyl citrate.

16. The controlled release minitablet of claim 14 wherein the plasticizer is acetyltributyl citrate.

17. The controlled release minitablet of claim 16 wherein the extended release polymer is ethylcellulose polymer.

18. A method of making controlled release minitablets comprising:
    feeding a carrier into a fluidized bed reactor;
    spraying a suspension comprising a homogeneous mixture of budesonide, acid, a plasticizer, and an extended release polymer onto the carrier to produce a granulated mixture;
    milling the granulated mixture;
    compressing the granulated mixture into extended release cores; and
    coating the extended release cores with a pH dependent delayed release coating to produce a controlled release minitablet, wherein the pH dependent delayed release coating comprises an anionic carboxylic polymer that is soluble in water at a pH of about 4 to about 8 and insoluble at a pH of about 1 to about 3, and wherein the pH dependent delayed release coating is in direct contact with the homogeneous mixture of the extended release cores.

19. The method of claim 18 further comprising blending the milled granulated mixture with at least one lubricant, at least one disintegrant, or combinations thereof prior to the compression step.

20. The method of claim 18 wherein the plasticizer is selected from the group consisting of acetyltributyl citrate, acetyltriethyl citrate, dibutyl sebacate, tri-n-butyl citrate, and triethyl citrate.

21. The method of claim 18 wherein the plasticizer is acetyltributyl citrate.

22. The method of claim 21 wherein the extended release polymer is ethylcellulose polymer.

* * * * *